United States Patent [19]
Caspari et al.

[11] Patent Number: 5,522,820
[45] Date of Patent: Jun. 4, 1996

[54] METHOD AND APPARATUS FOR SUTURING TISSUE

[75] Inventors: Richard B. Caspari, Maidens, Va.; Jason Lee, Diamond Bar; David C. Buboltz, Rancho Cocamango, both of Calif.

[73] Assignee: Arthrotech, Ontario, Calif.

[21] Appl. No.: 336,832

[22] Filed: Nov. 9, 1994

Related U.S. Application Data

[63] Continuation-in-part of Ser. No. 4,937, Jan. 15, 1993, abandoned.

[51] Int. Cl.⁶ .................................................. A61B 17/04
[52] U.S. Cl. ............................ 606/148; 606/139; 606/144
[58] Field of Search .............................. 606/139, 144–148

[56] References Cited

U.S. PATENT DOCUMENTS

| | | | |
|---|---|---|---|
| 1,577,054 | 3/1926 | Berkmann | 606/144 |
| 1,635,066 | 7/1927 | Wells | 606/146 |
| 2,286,578 | 6/1942 | Sauter . | |
| 2,434,133 | 1/1948 | Volk . | |
| 2,577,240 | 12/1951 | Findley . | |
| 4,467,801 | 8/1994 | Whiteside . | |
| 4,890,615 | 1/1990 | Caspari et al. | 606/146 |
| 4,923,461 | 5/1990 | Caspari et al. | 606/146 |
| 4,957,498 | 9/1990 | Caspari et al. | 606/146 |
| 5,059,201 | 10/1991 | Asnis | 606/144 |
| B1 4,890,615 | 11/1993 | Caspari et al. | 606/146 |

FOREIGN PATENT DOCUMENTS 630693  10/1949  United Kingdom .

*Primary Examiner*—Gary Jackson
*Attorney, Agent, or Firm*—Harness, Dickey & Pierce

[57] ABSTRACT

A method and apparatus for use in suturing tissue using a suture material. The apparatus includes first and second clamping members which are able to draw the suture material through the tissue. The apparatus further includes a handle portion which is used to remotely actuate the first and second clamping members.

22 Claims, 8 Drawing Sheets

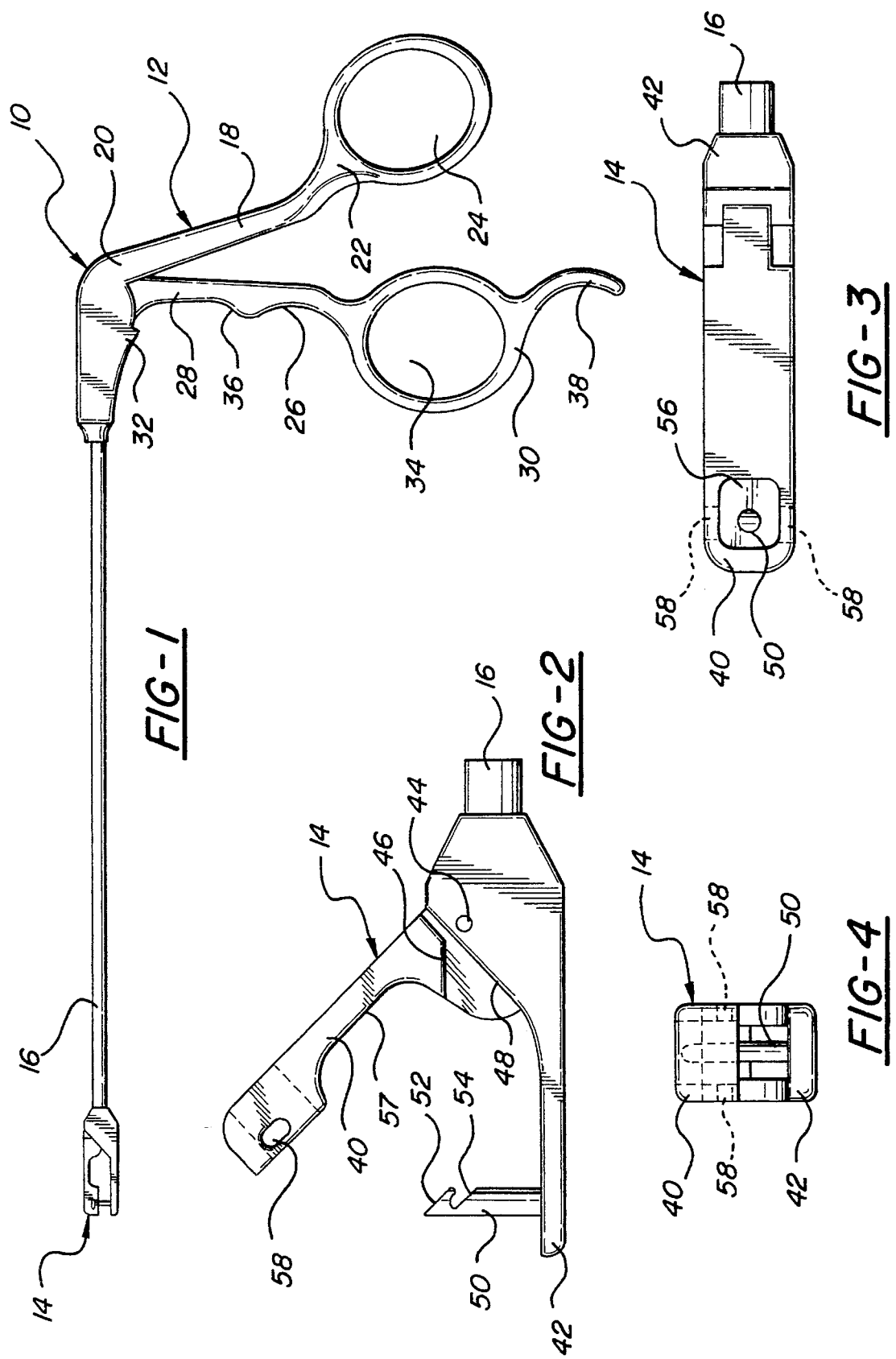

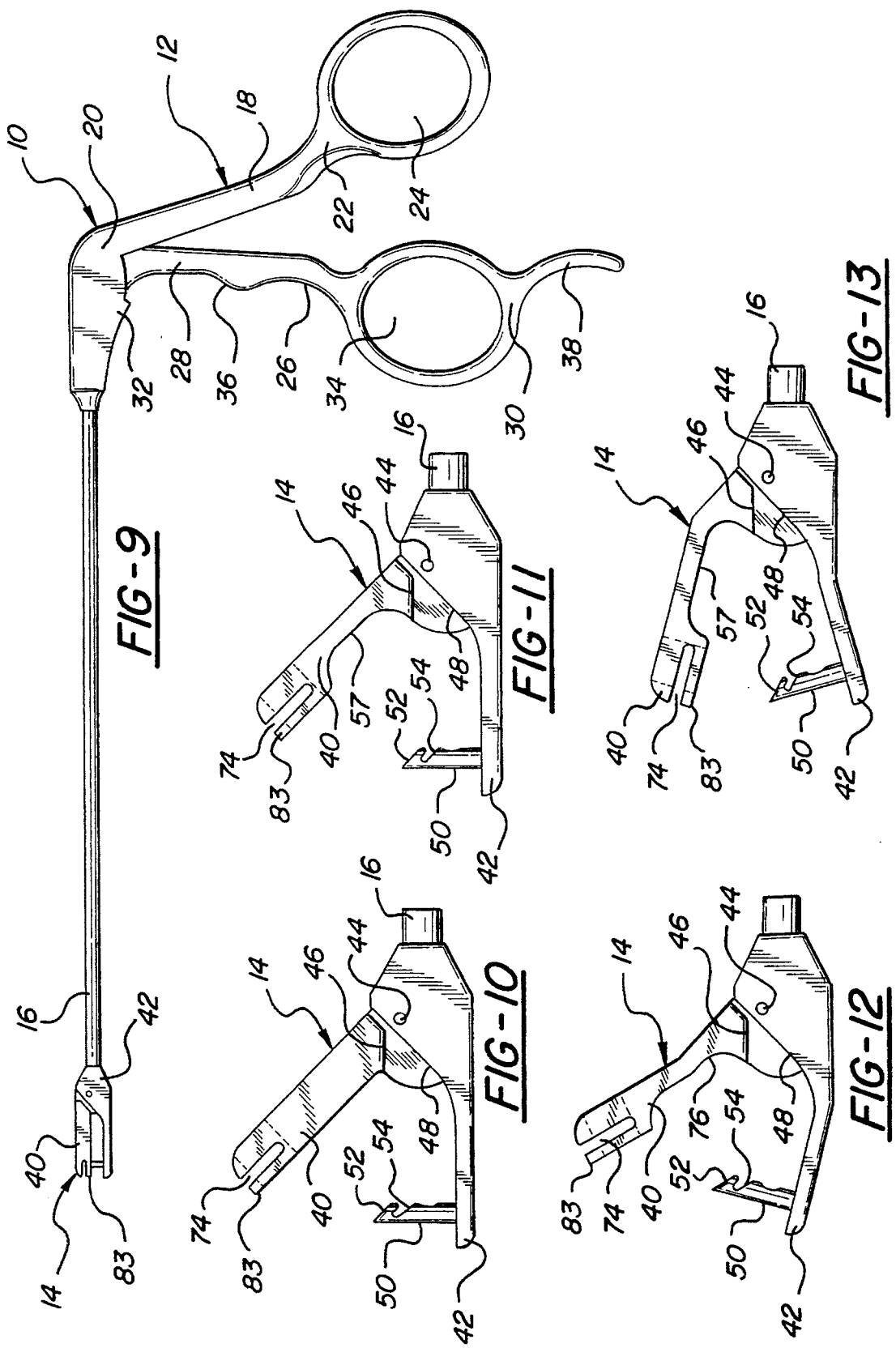

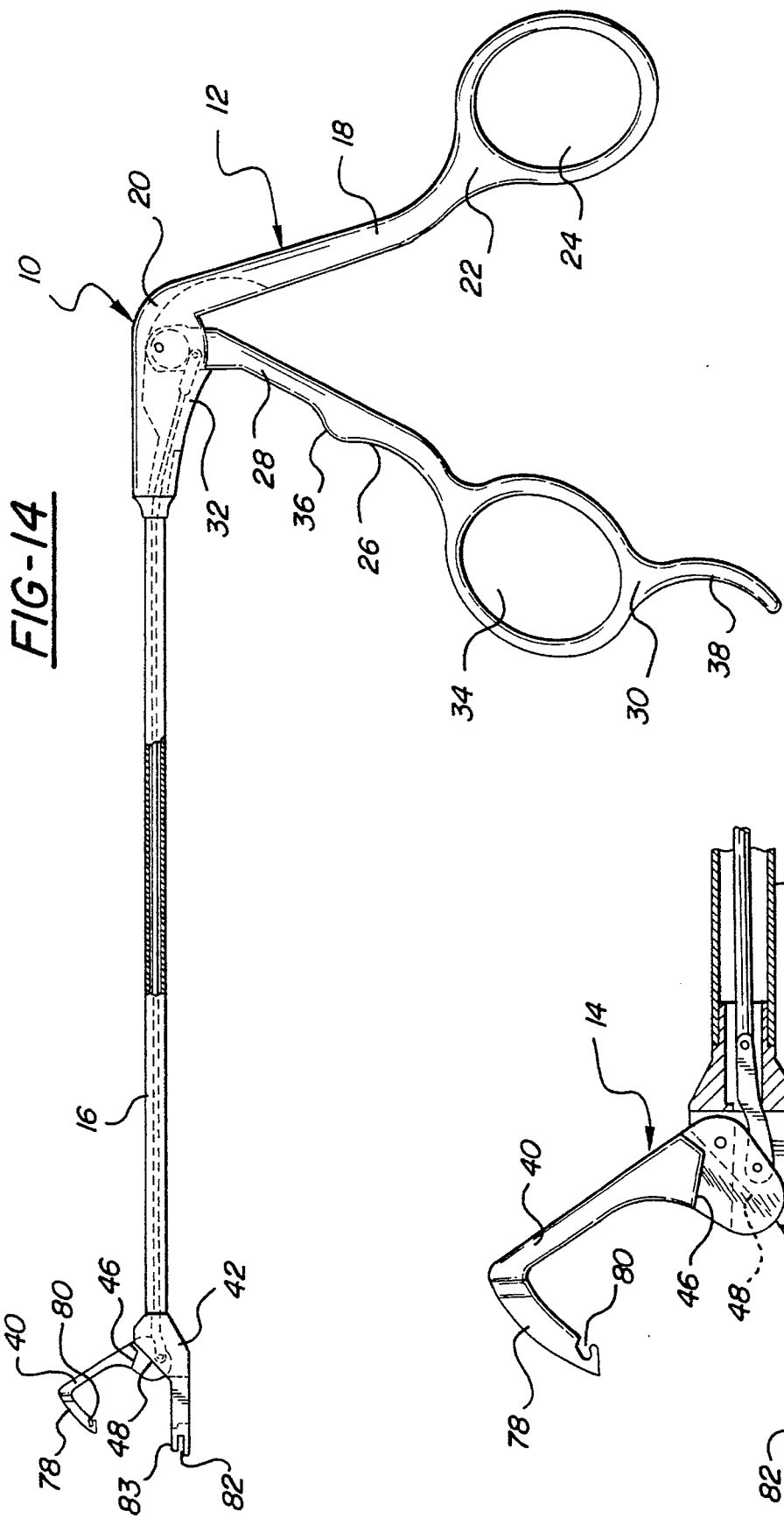

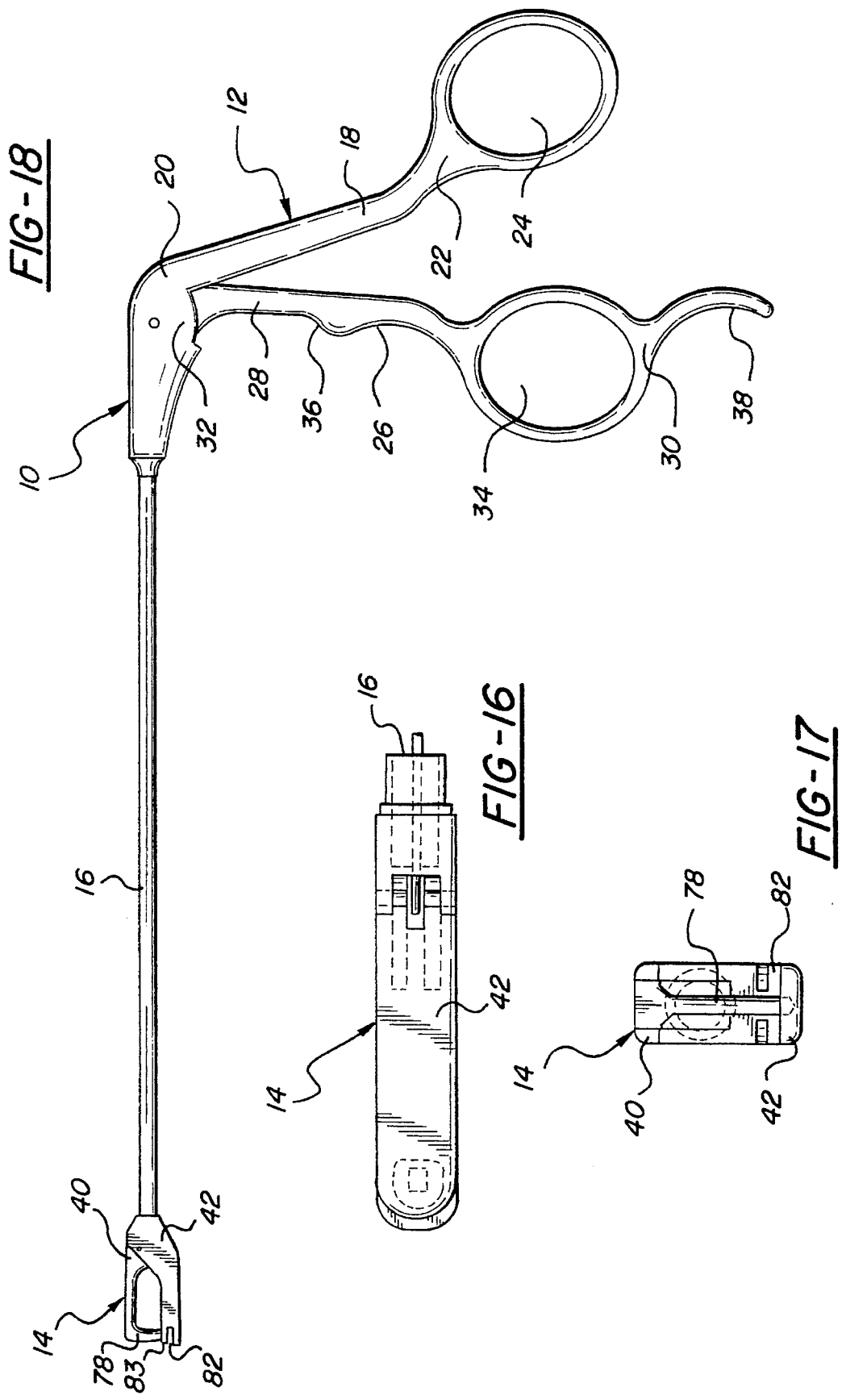

METHOD AND APPARATUS FOR SUTURING TISSUE

This is a continuation-in-part of U.S. Ser. No. 08/004,937 filed Jan. 15, 1993, now abandoned, entitled "Method and Apparatus for Suturing Tissue".

BACKGROUND OF THE INVENTION

The present invention relates generally to surgical instruments and procedures, and more particularly to a method and apparatus for suturing tissue.

One feature associated with the evolving field of medical technology is the continual effort to develop methods for repairing human tissue which require less disruption of the tissues and organs which surround an area requiring repair. In this regard, various forms of orthopedic surgery that once required that a large portion of a joint to be exposed during surgery can now be performed by making several small incisions. During such surgery, a fiber optic probe and various instruments are inserted into the incision to allow a surgeon to inspect and/or remove the damaged tissue without unduly damaging the surrounding non-injured tissue. This type of surgery is generally known as arthroscopic surgery.

While arthroscopic surgery when available is often the preferred form of surgery because of its less intrusive nature, there are certain difficulties which the surgeon may encounter during such surgery. One problem is that suturing tissue during arthroscopic surgery is somewhat difficult because a surgeon must manipulate the suturing instruments through a relatively small incision. One device which has been developed for facilitating suturing during arthroscopic surgery is the Shutt suture punch manufactured by Concept Incorporated. This particular instrument has a cannulated or hollow needle secured to a jaw positioned near the end of a long tube. The jaw can be manipulated by a hand grip to press the needle through the tissue to be sutured. Suture material is then fed through the tube from a spool attached to the hand grip into the hollow needle and therefore through the tissue. Enough suture material is advanced through the needle so that when the needle is withdrawn from the tissue and the instrument is removed from the incision, a portion of the suture material remains within the tissue. The suture material is then tied in a manner well-known in the art so as to secure the suture material to the tissue.

While this instrument is generally effective in suturing tissue, there are several disadvantages with respect to the use of this instrument. For example, the instrument requires manually advancing the suture material through the needle by manipulating the spool which is often somewhat difficult to do during surgery. In addition, the surgeon must verify that enough suture material has been advanced through the needle so that when the instrument is withdrawn from the incision, the suture material is not inadvertently pulled through the tissue. Furthermore, because the suture material must be fed up and through a hollow needle, tissue or other debris present in the surgical site may block the opening in the needle making it difficult to pass the suture material through the needle. In addition, because rotating the spool against the braided suture material tended to cause the braided suture material to expand such that it was unable to pass through the tube, only monofilament suture material can generally be used. This is disadvantageous because braided suture material is generally stronger than monofilament suture material. Finally, this particular instrument cannot generally be used to simultaneously pass several segments of suture material through the tissue which is required for certain types of sutures such as a mattress suture.

SUMMARY OF THE INVENTION

According to one embodiment of the present invention, an apparatus for use in suturing tissue is provided. The apparatus includes means for drawing suture material through the tissue. In addition, the apparatus includes means for remotely actuating the means for drawing the suture material through the tissue.

According to another embodiment of the present invention, a method is provided for suturing tissue using a surgical instrument having first and second members. The method comprises the steps of supporting the suture material by the first member. The second member is then brought into a position proximate to the first member so as to cause the second member to capture the suture material. The suture material is then drawn through the tissue upon relative displacement between the first and second members.

An advantage of the present invention is to provide a method and apparatus for suturing tissue in a relatively non-intrusive manner which is simple to use and requires fewer surgical steps to transport suture material through the tissue than existing instruments.

A further advantage of the present invention is to provide a method and apparatus for suturing tissue in a relatively non-intrusive manner wherein suture material is drawn through the tissue by a relatively simple manipulation of the hand grip of the apparatus.

A further advantage of the present invention is to provide a method and apparatus for suturing tissue in a relatively non-intrusive manner which is relatively resistant to clogging because of tissue and other debris which may be present in the surgical site.

Still another advantage of the present invention is to provide a method and apparatus for suturing tissue which is adaptable to provide a plurality of sutures with a single manipulation of the apparatus.

A further advantage of the present invention is to provide a method and apparatus for suturing tissue which is able to use either monofilament suture material or braided suture material.

Another advantage of the present invention is to provide a method and apparatus for suturing tissue which is relatively simple in construction and is relatively low in cost.

BRIEF DESCRIPTION OF THE DRAWINGS

Various additional advantages of the present invention will become apparent to one skilled in the art by reading the following specification and subjoined claims and by referencing the following drawings in which:

FIG. 1 is an elevational view of the apparatus for suturing tissue according to the first preferred embodiment of the present invention;

FIG. 2 is an enlarged elevational view of the suturing portion of the apparatus for suturing tissue shown in FIG. 1 according to the first preferred embodiment of the present invention;

FIG. 3 is an enlarged top elevational view of the suturing portion of the apparatus for suturing tissue shown in FIG. 1 according to the first preferred embodiment of the present invention;

FIG. 4 is an enlarged front elevational view of the suturing portion of the apparatus for suturing tissue shown in FIG. 1 according to the first preferred embodiment of the present invention;

FIG. 9 is an elevational view of the apparatus for suturing tissue according to another embodiment of the present invention;

FIG. 10 is an enlarged elevational view of the suturing portion of the apparatus for suturing tissue shown in FIG. 9 according to a preferred embodiment of the present invention;

FIG. 11 is an enlarged elevational view of the suturing portion of the apparatus for suturing tissue shown in FIG. 9 having a relief area for receiving tissue;

FIG. 12 is an enlarged elevational view of the suturing portion of the apparatus for suturing tissue shown in FIG. 9 having a relief area as well as having the second clamping member angled upwardly;

FIG. 13 is an elevational view of the suturing portion of the apparatus for suturing tissue shown in FIG. 13 having a relief area as well as having the second clamping member angled in a downward direction;

FIG. 14 is an elevational view of the apparatus for suturing tissue according to another preferred embodiment of the present invention;

FIG. 15 is an enlarged elevational view of the suturing portion of the apparatus for suturing tissue shown in FIG. 14 according to a preferred embodiment of the present invention;

FIG. 16 is a top elevational view of the suturing portion of the apparatus for suturing tissue shown in FIG. 14 in which the first clamping member is displaced in a direction toward the second clamping member;

FIG. 17 is a front elevational view of the apparatus for suturing tissue shown in FIG. 14 with the first clamping member displaced towards the second clamping member; and FIG. 18 is a front elevational view of the apparatus for suturing tissue shown in FIG. 14 with the first clamping member directed toward the second clamping member.

DETAILED DESCRIPTION OF THE PREFERRED EMBODIMENTS

Figure 5A:
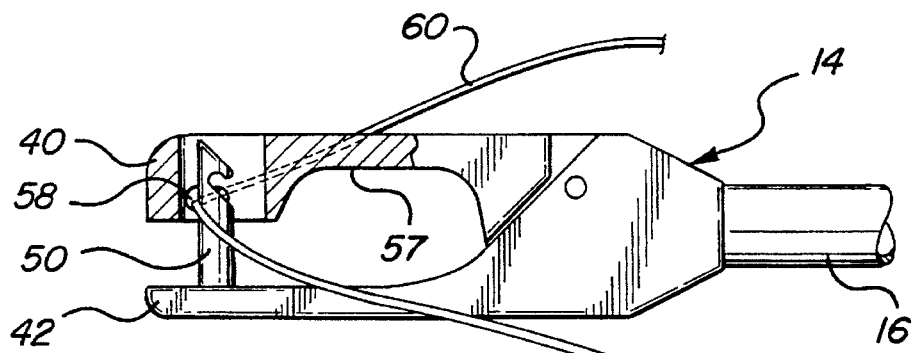
FIG. 5A is an enlarged side elevational view, partially broken away, of the suturing portion shown in FIG. 2 immediately prior to being inserted into an incision according to the method of the preferred embodiment of the present invention.

It should be understood that while this invention is described in connection with several particular examples thereof, the scope of the invention need not be so limited. Rather, those skilled in the art will appreciate that the following teachings can be used in a much wider variety of applications than the examples specifically mentioned herein.

Referring to FIG. 1, the apparatus 10 is shown according to the teachings of the first preferred embodiment of the present invention. The apparatus 10 is used for suturing various forms of tissue during surgery. For example, the apparatus 10 may be used to suture ligaments, tendons, muscles as well as other forms of soft tissue. In addition, while the apparatus 10 may be used during arthroscopic surgery, it will also be appreciated that the apparatus 10 may be used to suture tissue during other surgical procedures such as when access to the site of the suture is limited.

The apparatus 10 comprises an actuating portion 12 and a suturing portion 14. The suturing portion 14 is used to provide means for drawing suture material through the tissue once the suturing portion 14 has engaged the tissue. The actuating portion 12 is used to remotely actuate the suturing portion 14. The actuating portion 12 and the suturing portion 14 are connected by a tubular member 16 which is used to carry an actuating rod which is more fully described below. While the tubular member 16 is shown as being straight, it will be appreciated that the tubular member 16 may be curved to facilitate access to the tissue. In this regard, the tubular member 16 may be curved either to the left or right between 15° to 45° or it may be curved such that the suture portion 14 extends upwardly from the actuating portion 12 by between 7.5° and 15°. Alternatively, it may be desirable to angularly displace the suturing portion 14 (such as by 15°) rather than the tubular member 16 to achieve substantially the same result. The structure and operation of the actuating portion 12 and the suturing portion 14 will now be described in greater detail.

The actuating portion 12 includes a generally fixed handle portion 18 which has a first end 20 and a second end 22. The first end 20 of the fixed handle portion 18 is used to connect the fixed handle portion 18 to the tubular member 16. The second end 22 of the fixed handle portion 18 has a thumb opening 24 formed therein which assists the surgeon in grasping the apparatus 10.

The actuating portion 12 further includes a movable handle portion 26 having a first end 28 and a second end 30. The first end 28 of the movable handle portion 26 is attached on the inside angled surface 32 of the fixed handle portion 18 and is operable to pivot in a direction toward and away from the fixed handle portion 18. The movable handle portion 26 also includes an opening 34 formed near the second end 30 through which a surgeon may insert a finger while grasping the apparatus 10. The movable handle portion 26 further includes the contoured surfaces 36 and 38 which are able to receive the surgeon's fingers so as to provide a relating comfortable and secure grip for the surgeon using the apparatus 10.

The suturing portion 14 of the apparatus 10 will now be described with reference to FIGS. 2–4. The suturing portion 14 of the apparatus 10 is shown as being connected to the tubular member 16 and having a first clamping member 40 and a second clamping member 42. The first clamping member 40 is mounted so as to provide a pivoting movement with respect to the second clamping member 42 by means of the pin 44. The first clamping member 40 is also formed with a shoulder 46 which, in the closed or clamped position, engages the surface 48 of the first clamping member 40 thereby limiting the pivoting movement of the first clamping member 40 in the closed or clamped position. The first clamping member 40 is approximately 0.123" in thickness, while the second clamping member 42 is approximately 0.051" in thickness. Finally, the suturing portion 14 is approximately 0.827" in length.

The first clamping member 40 is connected to the movable handle portion 26 by an actuating rod (not shown) which is disposed within the tubular member 16. The actuating rod is connected via pins (not shown) such that pivoting movement of the movable handle portion 26 in a direction away from the fixed handle portion 18 causes the first clamping member 40 to be displaced in a direction away from the second clamping member 42. In a similar fashion, a pivoting movement of the movable handle portion 26 in a direction toward the fixed handle portion 18 causes the first clamping member 40 to be brought into a position proximate to the second clamping member 42. Accordingly, when tissue is disposed between the first and second clamping members 40 and 42, the first clamping member 40 may be used to force the tissue against the second clamping member 42.

To provide means for penetrating the tissue and drawing the suture material through the tissue, the second clamping member 42 further includes a needle member 50. The needle member 50 is shown as having a generally round 0.047" cross-section with an angled upper surface 52. In addition, the needle member 50 extends approximately 0.224" above the second clamping member 42. Furthermore, the needle member 50 further includes a hook-shaped recess 54 which is disposed on the side of the needle member 50 opposite the apex of the angled upper surface 52 at a position adjacent to the angled upper surface 52. As will be more fully discussed below, the hook-shaped recess 54 is used to capture the suture material so as to draw the suture material through the tissue when the second clamping member 42 is displaced from the first clamping member 40.

Formed within the first clamping member 40 is an opening 56 as shown in FIG. 3. The opening 56 provides a relief area for the tissue as it is clamped between the first clamping member 40 and the second clamping member 42. In a similar fashion, the first clamping member 40 has a relief area 57 disposed on its side also to provide additional relief for tissue as it is clamped between the first clamping member 40 and the second clamping member 42. In addition, the first clamping member 40 further includes two apertures 58 formed in the sides of the first clamping member 40. The apertures 58 allow suture material to be supported by the first clamping member 40 in a manner more fully described below. The apertures 58 are positioned on the first clamping member 40 so as to allow the suture material to be easily threaded through the apertures 58 and in front of the surface of the needle member 50.

As will be appreciated by those skilled in the art, when suture material has been disposed within the apertures 58 of the first clamping member 40, the needle member 50 is able to capture the suture material when the second clamping member 42 is brought into a position proximate to the first clamping member 40. Because the suture material is captured by the needle member 50, subsequent displacement of the second clamping member 42 with respect to the first clamping member 40 causes the needle member 50 to draw suture material from the first clamping member 40. Because the tissue which is to be sutured is located between the first and second clamping members 40 and 42, this relative displacement between the first and second clamping members 40 and 42 causes the suture material to be drawn through the tissue.

Figure 5B:
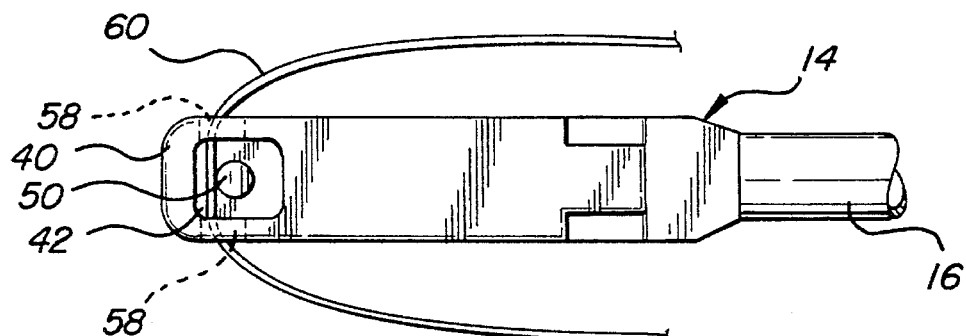
FIG. 5B is a top elevational view of the suturing portion shown in FIG. 2 immediately prior to being inserted into an incision according to the method of the preferred embodiment of the present invention.

The method according to the preferred embodiment of the present invention will now be described with reference to FIGS. 5A–5F. After the necessary preoperative and operative procedures have been performed prior to suturing, the suture material 60 initially is threaded through the apertures 58 in the first clamping member 40 and around the needle member 50 on the side opposite the hook-shaped recess 54. It is important that in the starting position the suture material 60 be positioned on the opposite side of the needle member 50 as this allows the first clamping member 40 to be opened without capturing the suture material 60 within the hook-shaped recess 54. The suture material 60 may be either monofilament suture material or braided suture material. In addition, the suture material 60 may be #2 to 2-0. Once the suture material 60 is supported by the first clamping member 40 in this manner, the apparatus 10 is inserted through a relatively small incision in the patient's body with suturing portion 14 closed as shown in FIGS. 5A and 5B.

Figure 5C:
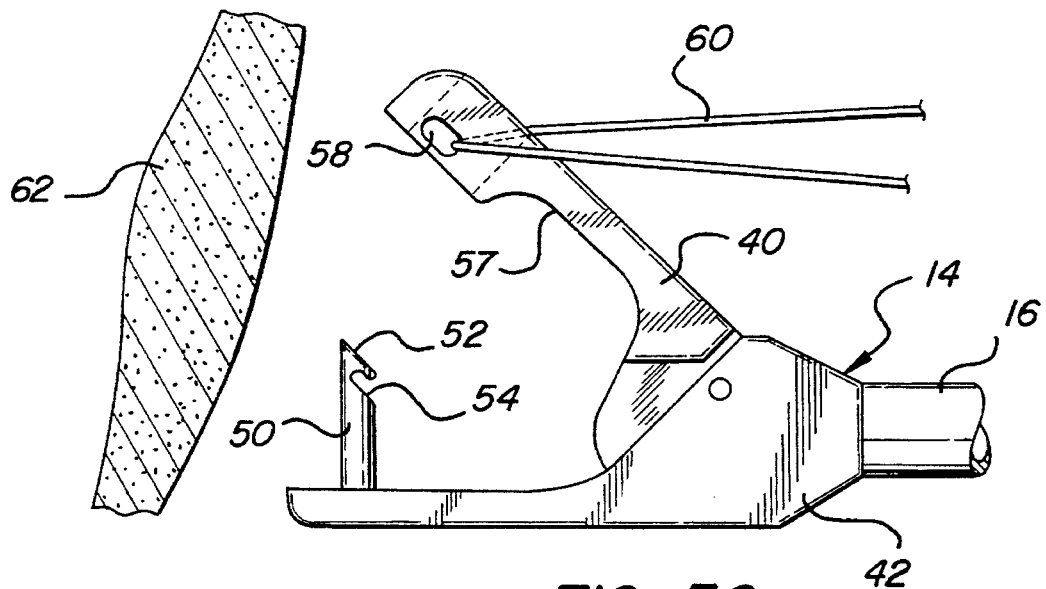
FIG. 5C is a side elevational view of the suturing portion shown in FIG. 2 immediately prior to engaging the tissue which is to be sutured according to the method of the preferred embodiment of the present invention.
Figure 5D:
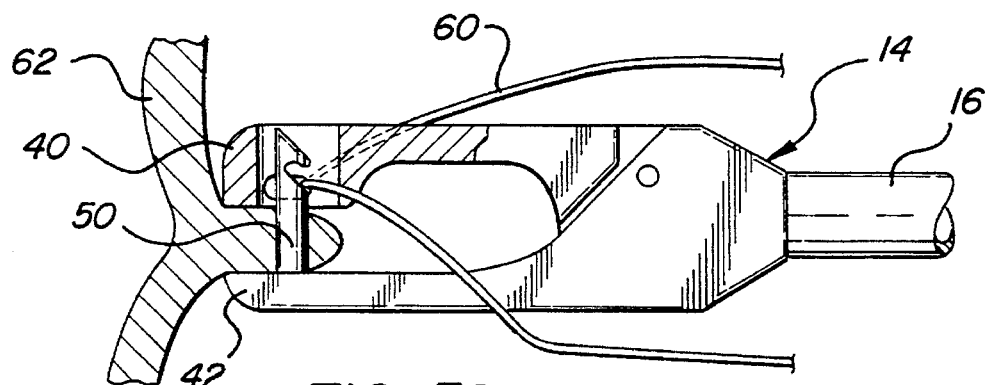
FIG. 5D is a side elevational view of the suturing portion shown in FIG. 2 engaging the tissue which is to be sutured according to the method of the preferred embodiment of the present invention.
Figure 5E:
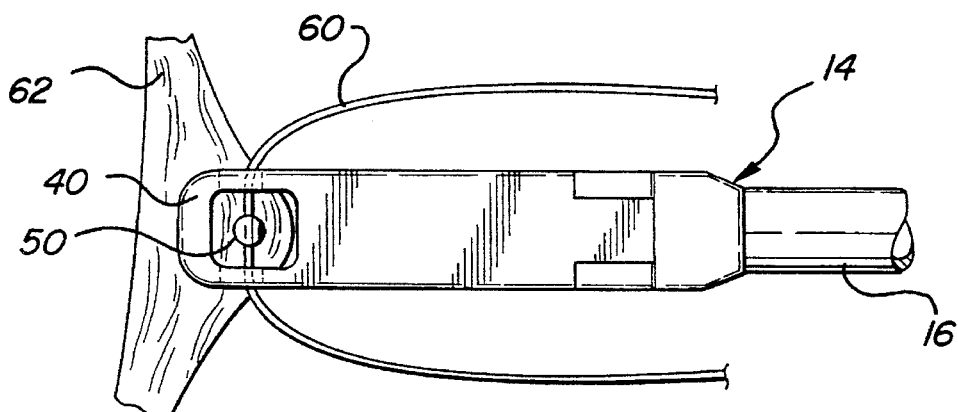
FIG. 5E is a top elevational view of the suturing portion shown in FIG. 2 engaging the tissue which is to be sutured according to the method of the preferred embodiment of the present invention.
Figure 5F:
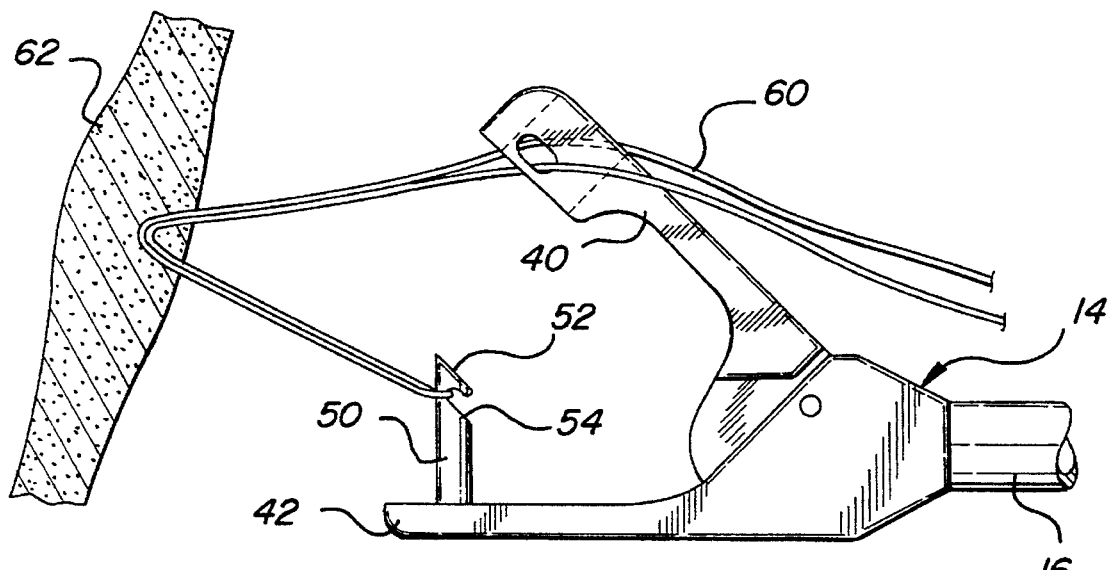
FIG. 5F is a side elevational view of the suturing portion shown in FIG. 2 after being disengaged from the tissue which is to be sutured according to the method of the preferred embodiment of the present invention.

Once within the patient's body, the surgeon positions the apparatus 10 with the suturing portion 14 closed adjacent to the tissue 62 which is to be sutured. Once the surgeon has positioned the suturing portion 14 adjacent to the tissue 62, the surgeon opens the suturing portion 14 as shown in FIG. 5C by displacing the movable handle portion 26 with respect to the fixed handle portion 18. The surgeon then closes the suturing portion 14 so as to engage the tissue 62 to be sutured by bringing the second clamping member 42 into a position proximate to the first clamping member 40 as shown in FIG. 5D. As this occurs, the needle member 50 penetrates the tissue 62 in the area which is to be sutured. After the needle member 50 completely penetrates the tissue 62, the suture material 60 disposed between the apertures 58 in the first clamping member 40 is captured by the hook-shaped recess 54 of the needle member 50 as shown in FIGS. 5D and 5E. Accordingly, as the first clamping member 40 is subsequently displaced from the second clamping member so as to disengage the tissue 62 as shown in FIG. 5F, the suture material 60 which is captured in the hook-shaped recess 54 is drawn through the tissue 62. The surgeon may then remove the apparatus 10 from the incision and then secure the suture material 60 in a manner well-known to those skilled in the art.

Figure 6:
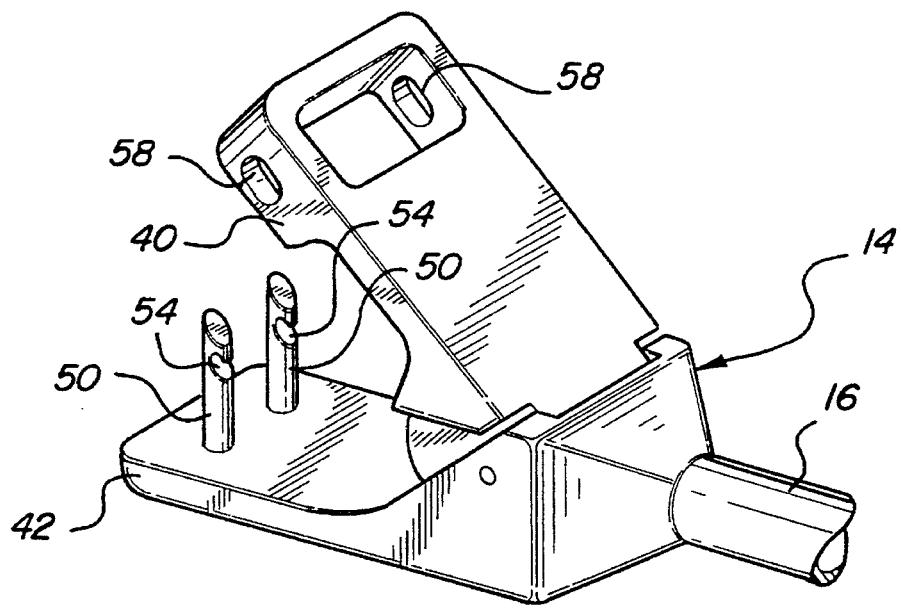
FIG. 6 is a perspective view of the apparatus for suturing tissue according to the second preferred embodiment of the present invention.

The second preferred embodiment of the present invention will now be described with reference to FIG. 6 in which similar reference numerals are used to describe similar elements discussed with respect to the first preferred embodiment of the present invention. The second clamping member 42 according to the second preferred embodiment includes two needle members 50 which are spaced laterally adjacent to each other. Each of the needle members 50 includes a hook-shaped recess 54 which are able to capture the suture material in a manner similar to that described above. The use of two needle members 50 allow a mattress suture to be disposed on the tissue in the following manner. As with the first preferred embodiment, the suture material is threaded through the apertures 58 in the first clamping member 40 adjacent to the needle member 50 on the side opposite the hook-shaped recess 54. When the surgeon displaces the first clamping member 40 to a position proximate to the second clamping member 42 to engage the tissue 62, both of the needle members 50 penetrate the tissue and capture the suture material 60. Upon subsequent displacement of the first clamping member 40 with respect to the second clamping member 42, the suture material 60 which is captured in hook-shaped recess 54 of each of the needle members 50 is drawn through the tissue 62. The surgeon then can withdraw the suturing portion 14 from the patient and secure the suture material 60 in a manner known to those skilled in the art. The resulting mattress suture is often preferred by surgeons as being more secure than the other suture described above.

Figure 7:
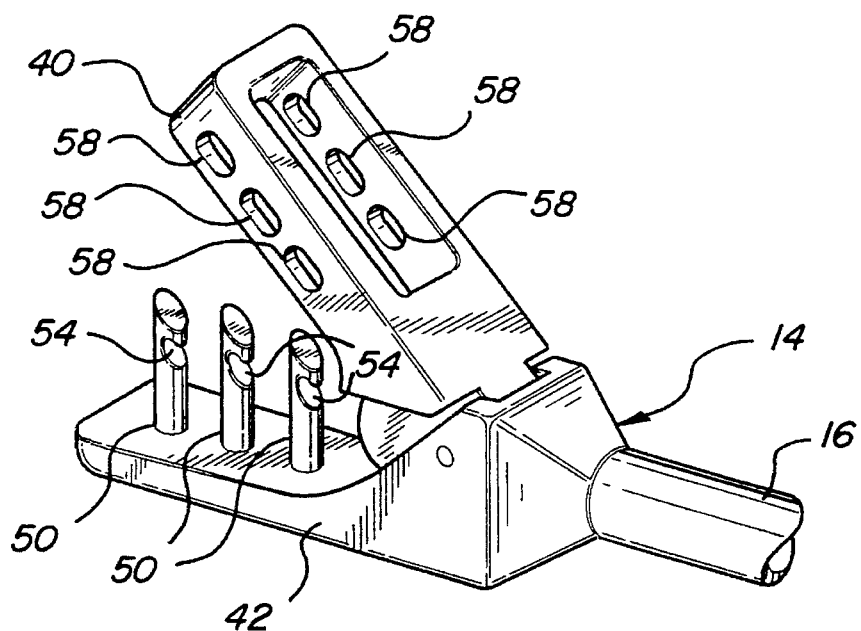
FIG. 7 is a perspective view of the apparatus for suturing tissue according to the third preferred embodiment of the present invention.

The third preferred embodiment of the present invention will now be described with reference to FIG. 7. In describing the third preferred embodiment, similar reference numerals will be used to describe elements which are similar to elements described in connection with the first preferred embodiment of the present invention. The third preferred embodiment of the present invention is able to produce two longitudinally spaced sutures by using three needle members 50. The needle members 50 are spaced longitudinally along the second clamping member 42 and each include a hook-shaped recess 54. To support the suture material 60 with respect to the first clamping member 40, the first clamping member 40 includes three pairs of longitudinally spaced apertures 58 each of which are operable to receive the suture material 60. The use of the apparatus 10 according to this embodiment is the same as described with respect to the other embodiments with the exception that three lengths of suture material 60 must be threaded through the apertures 58 prior to using the apparatus 10. Once the suture material 60 is disposed within the apertures 58, however, the suturing operation is performed in the same manner as described above with the result being two longitudinally spaced sutures being placed in the tissue 62.

Figure 8A:
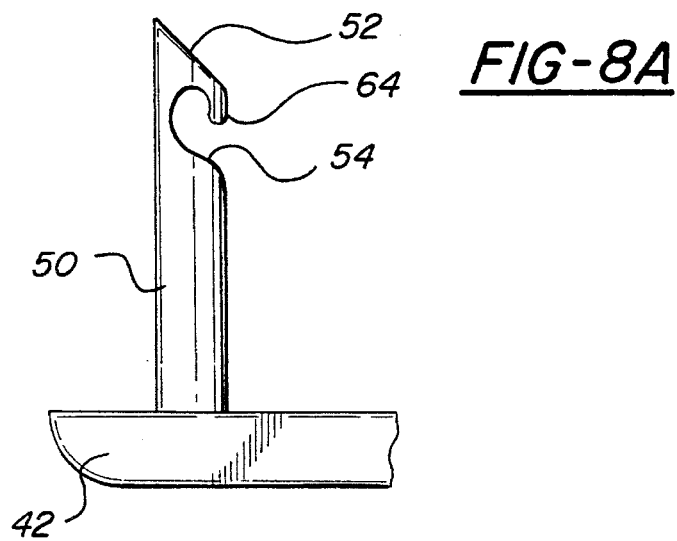
FIGS. 8A–E are elevational views of various alternative needle members which may be used with the method and apparatus for suturing tissue shown in FIG. 1 according to the preferred embodiments of the present invention.
Figure 8B:
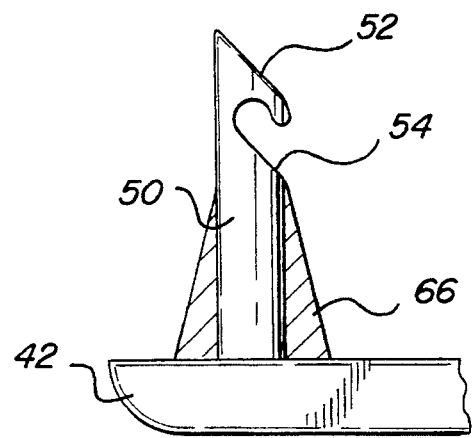
Figure 8C:
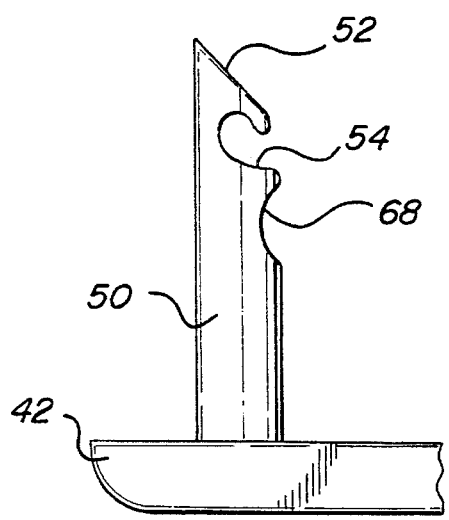

It will also be appreciated that the needle member 50 may also include means for facilitating withdrawal of the needle member 50 from the tissue. In this regard, the needle member 50 shown in FIG. 8A includes a rounded projection 64 disposed adjacent to hooked-shaped recess 54. The rounded projection 64 is designed to facilitate removal of the needle member 50 from the tissue by reducing the likelihood that tissue will bind against the needle member 50 as the needle member 50 is removed from the tissue. Alternatively, the needle member 50 may include a cone-shaped portion 66 as shown in FIG. 8B. The cone-shaped portion 66 is also used to facilitate removal of the needle member 50 from the tissue by reducing the tendency that the needle member 50 will bind against the tissue. Furthermore, the needle member 50 may alternatively include a second recess 68 as shown in FIG. 8C. The second recess 68 is located adjacent to the hook-shaped recess 54 and also serves to facilitate removal of the needle member 50 from the tissue by reducing the tendency of the tissue to bind against the needle portion 50.

Figure 8D:
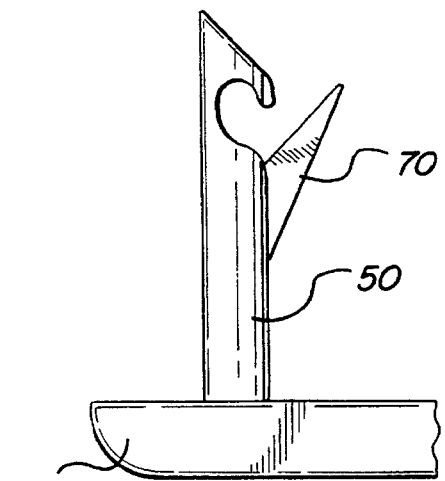
Figure 8E:
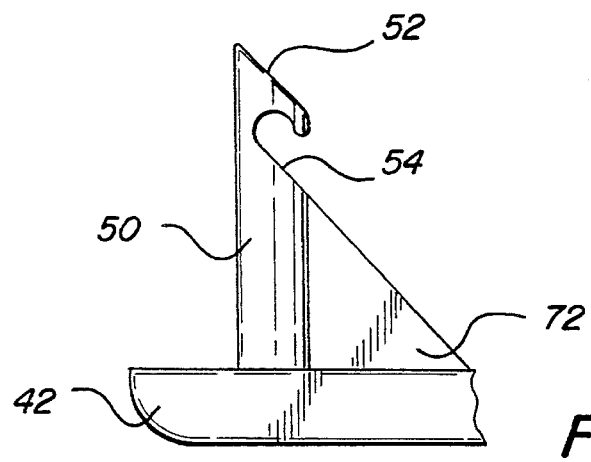

In addition, the means for facilitating withdrawal of the needle member 50 may be a blade member 70 which extends from the needle member 50 in the rearward and upward direction as shown in FIG. 8D. Furthermore, the means for facilitating withdrawal of the needle member 50 may also be a blade member 72 which angularly extends from the hook-shaped recess 54 at the rear of the needle member 50 in a downward direction to the second clamping member 42 as shown in FIG. BE.

Another preferred embodiment of the present invention will now be described with reference to FIGS. 9–13. In describing this preferred embodiment, similar reference numerals will be used to describe elements which are similar to elements described in connection with the first preferred embodiment of the present invention. As with the first preferred embodiment, the apparatus 10 comprises an actuating portion 12 and a suturing portion 14. The suturing portion 14 of the apparatus 10 is connected to the tubular member 16 and has a first clamping member 40 and a second clamping member 42. In the fourth preferred embodiment, however, the first clamping member 40 includes a slot 74 for receiving suture material instead of apertures 58 as shown with the first preferred embodiment. The slot 74 extends from a position proximal of the needle member 50 to the distal end of the first clamping member 40. Additionally, the slot 74 extends downwardly through the lip 83 to provide for generally unrestricted passage of the suture material.

During usage of the apparatus 10 according to the preferred embodiment shown in FIGS. 9–13, suture material is initially placed in the slot 74. When the surgeon displaces the first clamping member 40 to a position proximate to the second clamping member 42 to engage the tissue, the needle member 50 penetrates the tissue in the area which is to be sutured. The suture material disposed within the slot 74 in the first clamping member 40 is then captured by the hook-shaped recess 54 of the needle member 50. When the surgeon moves the first clamping member 40 to a position which is displaced from the second clamping member 42, the suture material is drawn through the tissue 62. As the surgeon removes the apparatus 10 from the incision, the suture material is pulled free from the slot 74 through the lip 83. The suture material is then secured in a manner well-known to those skilled in the art.

It will be appreciated that the lower surface of the first clamping member 40 shown in FIG. 10 is substantially straight so as to force the tissue against the second clamping member 42. Alternatively, the first clamping member 40 may be formed with a relief area 57 as shown in FIG. 11. The relief area 57 is able to receive tissue as it is clamped between the first clamping member 40 and the second clamping member 42. The relief area 57 may be formed of different shapes (such as the relief area 76 shown in FIG. 12) to accommodate different shapes and amounts of tissue. Additionally, as shown in FIGS. 12–13, second clamping member 42 may be angled upward or downward to accommodate for different types of tissues as well as different types of uses. Finally, as with the first preferred embodiment, the tubular member 16 may be curved to the left or to the right or upward and the suturing portion 14 may be angularly displaced to facilitate access to the tissue.

A further embodiment of the present invention will now be described with reference to FIGS. 14–17. In describing this embodiment, similar reference numerals will be used to describe elements which are similar to the elements described in connection with the first preferred embodiment of the present invention. As with the first preferred embodiment, the apparatus 10 comprises an actuating portion 12 and a suturing portion 14. The suturing portion 14 of the apparatus 10 is connected to the tubular member 16 and has a first clamping member 40 and a second clamping member 42. The first clamping member 40 includes a needle-shaped projection 78 which extends downwardly from the first clamping member 40. The needle-shaped projection 78 is operable to pierce tissue so as to engage and subsequently draw suture material through the tissue in a manner similar to that described above.

The needle-shaped projection 78 further includes a hook-shaped recess 80. The hook-shaped recess 80 is disposed at the lower end of the needle-shaped projection and is operable to receive suture material which is carried by the second clamping member 42. As will be appreciated by those skilled in the art, the hook-shaped recess 80, as well as the needle-shaped projection 78, may be of any suitable configuration.

The second clamping member 42 further includes a slot 82 which is disposed at the distal end of the second clamping member 42. The slot 82 is operable to receive suture material in a manner similar to that described above. In this regard, prior to entry into the patient's body, the first clamping member 40 and the second clamping member 42 are displaced towards one another and suture material is placed within the slot 82. Once located adjacent to the tissue which is to be sutured, the first clamping member 40 and the second clamping member 42 are displaced from each other and then are brought towards each other so as to allow the needle-shaped projection 78 to pierce the tissue. As the needle-shaped projection 78 pierces the tissue, the hook-shaped recess 80 captures the suture material so that subsequent movement of the first clamping member 40 in a direction away from the second clamping member 42 will cause the suture material to be withdrawn through the tissue.

It will be appreciated that the first clamping member 40 and the second clamping member 42 may be of any suitable configuration which is operable to perform the matter described above. In this regard, the first and second clamping members 40 and 42 may be angled upward or downward, or may be curved to the left or right depending on the particular need.

Specific embodiments of the invention have been shown and described in detail to illustrate the principles of the present invention. For example, additional needle members may be used to cause different types of sutures to be placed in the tissue. As other examples, slots instead of apertures may be present to receive suture material, and the clamping members may be of different configurations to facilitate the positioning of tissue for suturing. In addition, the present invention may be used in various surgical procedures which are not arthroscopic in nature such as in various obstetric procedures. It will be understood that the invention may be embodied in other forms without departing from such principles and the fair scope of the present invention.

What is claimed is:

1. A suturing instrument for use in suturing tissue using a suture material, the suturing instrument comprising:

a first clamping member;

a second clamping member, said first and second clamping members being displaceable with respect to each other;

means for moving said first clamping member with respect to said second clamping member;

the suture material received by said second clamping member; and needle means fixed to said first clamping member, said needle means including:

(a) means for avoiding coupling of the needle means with the suture material when said first clamping member is initially brought into proximity with respect to said second clamping member; and (b) said needle means engaging the suture material upon subsequent movement of said first clamping member with respect to said second clamping member.

2. The apparatus according to claim 1, wherein said needle means comprises a needle member, said needle member being operable to draw said suture material through the tissue.

3. The apparatus according to claim 1, wherein said needle means comprises a plurality of needle members, each of said needle members being operable to draw said suture material through the tissue.

4. The apparatus according to claim 1, wherein said needle means comprises a slot for receiving said suture material.

5. The apparatus according to claim 1, wherein said first and second clamping members are disposed on said moving means such that the tissue is able to be disposed between said first and second clamping members.

6. The apparatus according to claim 1, wherein said needle means is operable to penetrate the tissue when said second member is brought into a position proximate to said first member.

7. The apparatus according to claim 6, wherein said needle means is operable to draw said suture material through the tissue when said second member is displaced from a position proximate to said first member.

8. The apparatus according to claim 1, wherein said needle means includes means for facilitating withdrawal of said needle means from said tissue.

9. The apparatus according to claim 8, wherein said means for facilitating withdrawal of said needle means from said tissue includes a cone-shaped member disposed on said needle means.

10. The apparatus according to claim 8, wherein said means for facilitating withdrawal of said needle means from said tissue includes a recess disposed on said needle means.

11. The apparatus according to claim 8, wherein said means for facilitating withdrawal of said needle means from said tissue includes a rounded projection disposed on said needle means.

12. The apparatus according to claim 11, wherein said means for facilitating withdrawal of said needle means from said tissue includes a blade member extending from said needle means.

13. The apparatus according to claim 12, wherein said second clamping member includes at least one aperture which is operable to support said suture material with respect to said first member.

14. The apparatus according to claim 12, wherein said needle means includes a hooked-shaped recess which is operable to capture said suture material when said second clamping member is brought into a position proximate to said first clamping member.

15. The apparatus according to claim 14, wherein said first clamping member further includes a second needle means, said second needle means being operable to draw said suture material through said tissue as said second clamping member is displaced from a position proximate to said first clamping member.

16. The apparatus according to claim 15, wherein said first clamping member further includes a third needle means, said third needle means being operable to draw said suture material through the tissue as said second clamping member is displaced from a position proximate to said first clamping member.

17. The apparatus according to claim 1, wherein said second clamping member includes a slot for receiving said suture material.

18. A method for suturing tissue with a suturing material using a surgical instrument having first and second clamping members, means for displacing said first and second clamping members with respect to one another, needle means fixed to the first clamping member, means for avoiding coupling of the needle means with the suture material, and said method comprising the steps of:

supporting said suture material on said second clamping member of said surgical instrument;

initially bringing said second clamping member into a position proximate said first clamping member and avoiding coupling of the suture material with said needle means;

subsequently bringing said second clamping member of said surgical instrument into a position proximate to said first clamping member so as to cause said needle means to capture said suture material; and drawing said suture material through the tissue by causing relative displacement between said first and second clamping members.

19. The method according to claim 18, wherein said step of subsequently bringing said second clamping member of said surgical instrument into a position proximate to said first clamping member includes the step of causing said needle means to penetrate the tissue before said suture material is captured by said clamping means.

20. The method according to claim 19, wherein said needle means includes a hooked-shaped recess, said step of subsequently bringing said second clamping member of said surgical instrument into a position proximate to said first clamping members includes the step of causing said hooked-shaped recess to capture said suture material.

21. The method according to claim 20, wherein said step of subsequently bringing said second clamping member of said surgical instrument into a position proximate to said first clamping member includes the step of causing a plurality of needle members to capture said suture material.

22. The method according to claim 21, further comprising the step of disposed said suture material in a slot.

\* \* \* \* \*

UNITED STATES PATENT AND TRADEMARK OFFICE
CERTIFICATE OF CORRECTION

PATENT NO. : 5,522,820

DATED : June 4, 1996

INVENTOR(S) : Richard B. Caspari, et al.

It is certified that error appears in the above-indentified patent and that said Letters Patent is hereby corrected as shown below:

Column 8, line 5, after "FIG.", delete "BE" and insert therefor --8E--.

Signed and Sealed this

Eighth Day of July, 1997

*Attest:*

*Attesting Officer*

BRUCE LEHMAN

*Commissioner of Patents and Trademarks*

UNITED STATES PATENT AND TRADEMARK OFFICE
CERTIFICATE OF CORRECTION

PATENT NO.   : 5,522,820
DATED        : June 4, 1996
INVENTOR(S)  : Caspari, Richard B., et al.

It is certified that error appears in the above-identified patent and that said Letters Patent is hereby corrected as shown below:

<u>Title page,</u>
Item [73], change "Assignee: Arthrotech, Ontario, Calif." to
-- Assignee: Arthrotek, Ontario, Calif. --.

Signed and Sealed this

Twenty-second Day of April, 2003

JAMES E. ROGAN
*Director of the United States Patent and Trademark Office*